(12) United States Patent
Lin et al.

(10) Patent No.: US 9,494,562 B2
(45) Date of Patent: Nov. 15, 2016

(54) METHOD AND APPARATUS FOR DEFECT DETECTION IN COMPOSITE STRUCTURES

(75) Inventors: Wei Lin, Singapore (SG); Lay Siong Goh, Singapore (SG);
(Continued)

(73) Assignee: Agency for Science, Technology and Research, Singapore (SG)

( * ) Notice: Subject to any disclaimer, the term of this patent is extended or adjusted under 35 U.S.C. 154(b) by 631 days.

(21) Appl. No.: 13/977,319

(22) PCT Filed: May 27, 2011

(86) PCT No.: PCT/SG2011/000196
§ 371 (c)(1),
(2), (4) Date: Sep. 4, 2013

(87) PCT Pub. No.: WO2012/091676
PCT Pub. Date: Jul. 5, 2012

(65) Prior Publication Data
US 2013/0338941 A1    Dec. 19, 2013

(30) Foreign Application Priority Data

Dec. 29, 2010  (SG) ............................... 201009706-1
Dec. 29, 2010  (SG) ............................... 201009708-7

(51) Int. Cl.
*G01N 29/44*    (2006.01)
*G01N 29/34*    (2006.01)
*G01N 29/46*    (2006.01)

(52) U.S. Cl.
CPC ........ *G01N 29/4427* (2013.01); *G01N 29/348* (2013.01); *G01N 29/4436* (2013.01);
(Continued)

(58) Field of Classification Search
CPC .............. G01N 29/348; G01N 29/4445; G01N 29/4427; G01N 229/0231; G01N
(Continued)

(56) References Cited

U.S. PATENT DOCUMENTS 4,462,082 A * 7/1984 Thiele ................ G01N 29/4463
367/13
4,545,251 A * 10/1985 Uchida .............. G01N 29/0609
73/1.82
(Continued)

FOREIGN PATENT DOCUMENTS

WO    WO-2010/103098 A1    9/2010

OTHER PUBLICATIONS

"International Application No. PCT/SG2011/000196, International Preliminary Report on Patentability dated Jul. 2, 2013", 10 pgs.
(Continued)

*Primary Examiner* — Carol S Tsai
(74) *Attorney, Agent, or Firm* — Schwegman Lundberg & Woessner, P.A.

(57) ABSTRACT

Methods and apparatus for non-destructive testing of a composite structure utilizing sonic or ultrasonic waves. In response to a wideband chirp wave sonic excitation signal transmitted from a probe to the composite structure, a probe signal received is correlated with a library of predetermined probe signals and a graphical representation of defects detected is generated. The graphical representation provides detailed information on defect type, defect location and defect shape. Also contemplated is a probe for non-destructive testing of a composite structure comprising three or more transducers wherein each transducer is separately configurable as a transmitter or as a receiver; and a controller coupled to each of transducer for providing signals thereto and receiving signals therefrom, wherein the signals pro-
(Continued)

vided thereto include signals for configuring each transducer as either a transmitter or a receiver, and signals for providing an excitation signal from each transducer which is configured as a transmitter.

18 Claims, 18 Drawing Sheets

(75) Inventors: Lye Seng Wong, Singapore (SG); Heng Kiat Jonathan Hey, Singapore (SG); Ricky Riyadi Chan, Singapore (SG); Roman Britner, Singapore (SG)

(52) U.S. Cl.
CPC .......... *G01N 29/4445* (2013.01); *G01N 29/46* (2013.01); *G01N 2291/0231* (2013.01); *G01N 2291/0427* (2013.01)

(58) Field of Classification Search
CPC ............................ 29/4436;G01N 29/46; G01N 2291/0427
USPC ............ 702/39; 73/631, 1.82, 628, 901, 594
See application file for complete search history.

(56) References Cited

U.S. PATENT DOCUMENTS

| | | | | |
|---|---|---|---|---|
| 5,146,289 | A * | 9/1992 | Newman | G01B 11/162 356/35.5 |
| 7,819,008 | B2 * | 10/2010 | Winter | G01B 17/02 702/33 |
| 8,834,376 | B2 * | 9/2014 | Stergiopoulos | A61B 8/0808 600/438 |
| 2004/0011132 | A1 | 1/2004 | Netzel | |
| 2005/0268720 | A1 * | 12/2005 | Quarry | G01N 29/041 73/627 |
| 2007/0056374 | A1 * | 3/2007 | Andrews | G01N 29/4418 73/628 |
| 2007/0084290 | A1 * | 4/2007 | Fetzer | G01N 29/0645 73/627 |
| 2007/0148999 | A1 * | 6/2007 | Haider | B06B 1/0629 439/67 |

OTHER PUBLICATIONS

"International Application No. PCT/SG2011/000196, Written Opinion mailed Aug. 8, 2011", 9 pgs.
"International Application No. PCT/SG2011/000196, International Search Report mailed Aug. 8, 2011", 7 pgs.

* cited by examiner

METHOD AND APPARATUS FOR DEFECT DETECTION IN COMPOSITE STRUCTURES

PRIORITY CLAIM TO RELATED APPLICATIONS

This application is a US National Stage application under 35 U.S.C. §371 of PCT/SG2011/000196, filed May 27, 2011, and published as WO 2012/091676 A1 on Jul. 5, 2012, which claims priority to Singapore Application No. 201009706-1, filed Dec. 29, 2010, and claims priority to Singapore Application No. 201009708-7, filed Dec. 29, 2010, which applications and publication are incorporated by reference as if reproduced herein and made a part hereof in their entirety, and the benefit of priority of each of which is claimed herein.

FIELD OF THE INVENTION

The present invention generally relates to non-destructive testing methods and apparatus, and more particularly relates to a method and apparatus for non-destructive testing from a single surface of a composite structure by utilizing sonic or ultrasonic waves.

BACKGROUND OF THE DISCLOSURE

Composite materials are increasingly being used for the inner and outer skins of commercial aircrafts. In order to meet the commercial aeronautics industry demands for airworthiness and flight safety, these new composite material structure require the development of new inspection technologies. Conventional inspection techniques include a so called "coin tap" testing method where the inspection conductor taps the suspected areas lightly with a hard and blunt tool to obtain indications of the underlying structure from the sound of the tap. Other testing methods include thermographic testing, non-linear spectroscopy, X-radiography, eddy current measurements and ultrasonic waves. Among these inspection methods, the ultrasonic wave method is the most commonly used testing method for non-destructive inspection of aircrafts. However, ultrasonic wave testing methods are not suitable for composite structures where non-isotropic properties of the composite structure materials cause high attenuation due to absorption and scattering.

Recent advances in sonic techniques such as pitch-catch method and resonance methods are able to obtain high sensitive responses from aircraft composite structures employing an excitation frequency lower than 100 kHz. In the pitch-catch method, a Lamb wave for composite structure inspection is generated and received by two respective piezoelectric probes located at a distance from each other on the surface of the composite. The behaviour of the Lamb wave in terms of wave mode, frequency, velocity, and level of attenuation is highly dependent on the material of the composite structure, the thickness of the laminate layers, and the material properties of the structure. Repeatable responses for complex composite structures are possible if the excitation signal is properly selected.

With respect to probe arrays for use with the pitch-catch method, various geometries have been proposed for the arrangement of transducers and the some prior art systems disclose multiple transducers in one probe device in which not all of the transducers are switched on or involved in nondestructive testing at the same time.

Commercially available Lamb wave-based testing apparati, however, are typically limited to two-dimensional location of defects and are conventionally not able to detect the presence of some types of defects, e.g., depth of delamination in carbon fiber composites. Further, when the presence of defects are detected, the such apparati do not provide a user-friendly way of identifying the various types of defects and do not enable an operator to differentiate between defects at different depths and defects of different types.

Thus, what is needed is a method and apparatus for Lamb wave-based non-destructive testing of composite structures which distinguishes between a variety of defects types not previously distinguishable and which provides a more user-friendly presentation of test results. Furthermore, other desirable features and characteristics will become apparent from the subsequent detailed description and the appended claims, taken in conjunction with the accompanying drawings and this background of the disclosure.

SUMMARY OF THE INVENTION

According to the Detailed Description, method for non-destructive testing of a composite structure is provided. The method includes providing a wideband chirp wave sonic signal to the composite structure for a predetermined time, a predetermined amplitude and a predetermined frequency as an excitation signal, and correlating a probed signal received from the composite structure with a library of predetermined probed signals. The method also includes outputting a graphical representation of defects detected, wherein the graphical representation of the defects detected conveys defect location information.

In addition, an apparatus for non-destructive testing of a composite structure is provided. The apparatus includes a transmitter, a receiver, a user interface, a storage device and a controller, which includes the function of excitation signal amplification. The transmitter provides a wideband chirp wave sonic signal to the composite structure for a predetermined time, a predetermined amplitude and a predetermined frequency as an excitation signal. The receiver receives a probed signal from the composite structure in response to the excitation signal. The user interface presents a graphical representation of defects detected and the storage device stores a library of predetermined probed signals. The controller is coupled to the receiver, the storage device and the user interface for correlating the probed signal received with the library of predetermined probed signals and providing signals to the user interface for outputting a graphical representation of defects detected conveying defect location information.

Further, probe for non-destructive testing of a composite structure is provided. The probe includes three or more transducers and a controller. The three or more transducers are each separately configurable as a transmitter or as a receiver. The controller is coupled to each of the three or more transducers and provides signals to each of the transducers and receiving signals from each of them. The signals provided by the controller include signals for configuring the transducers as either a transmitter or a receiver and signals for providing an excitation signal having a predetermined time, a predetermined amplitude and a predetermined frequency from each of the three or more transducers which is configured as a transmitter.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with the present invention.

FIG. 2, comprising FIGS. 2A and 2B, is a reference composite structure for use with the apparatus of FIG. 1 wherein FIG. 2A is a left, top front perspective of the reference composite structure and FIG. 2B is a front cross-sectional view of the reference composite structure;

FIG. 7, comprising FIGS. 7A and 7B, are graphical depictions of the received probe signal in the complex plane of the second conventional non-destructive composite structure testing system of FIG. 6 wherein FIG. 7A is a graph of the received probe signal when no disband defect is detected in the composite structure portion being tested and FIG. 7B is a graph of the received probe signal when a disband defect is detected in the composite structure portion being tested;

FIG. 10, comprising FIGS. 10A, 10B and 10C, are signaling diagrams of the wideband chirp excitation sweep signal of the non-destructive composite structure testing method of FIG. 8 in accordance with the present embodiment wherein FIG. 10A depicts the excitation sweep signals in accordance with the present embodiment from twenty kilohertz (20 kHz) to 40 kilohertz (40 kHz) within a predetermined time of three milliseconds (3 ms), FIG. 10B depicts the excitation sweep signals in accordance with the present embodiment from 40 kilohertz (40 kHz) to twenty kilohertz (20 kHz) within a predetermined time of three milliseconds (3 ms) in the time domain, and FIG. 10C depicts the excitation sweep signals in accordance with the present embodiment from 40 kilohertz (40 kHz) to twenty kilohertz (20 kHz) within a predetermined time of three milliseconds (3 ms) in the frequency domain;

FIG. 13 comprises FIGS. 13A and 13B, wherein

Skilled artisans will appreciate that elements in the figures are illustrated for simplicity and clarity and have not necessarily been drawn to scale. For example, the dimensions of some of the elements in the figures illustrating the probe may be exaggerated relative to other elements to help to improve understanding of embodiments of the present invention.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description of the invention.

Figure 1:
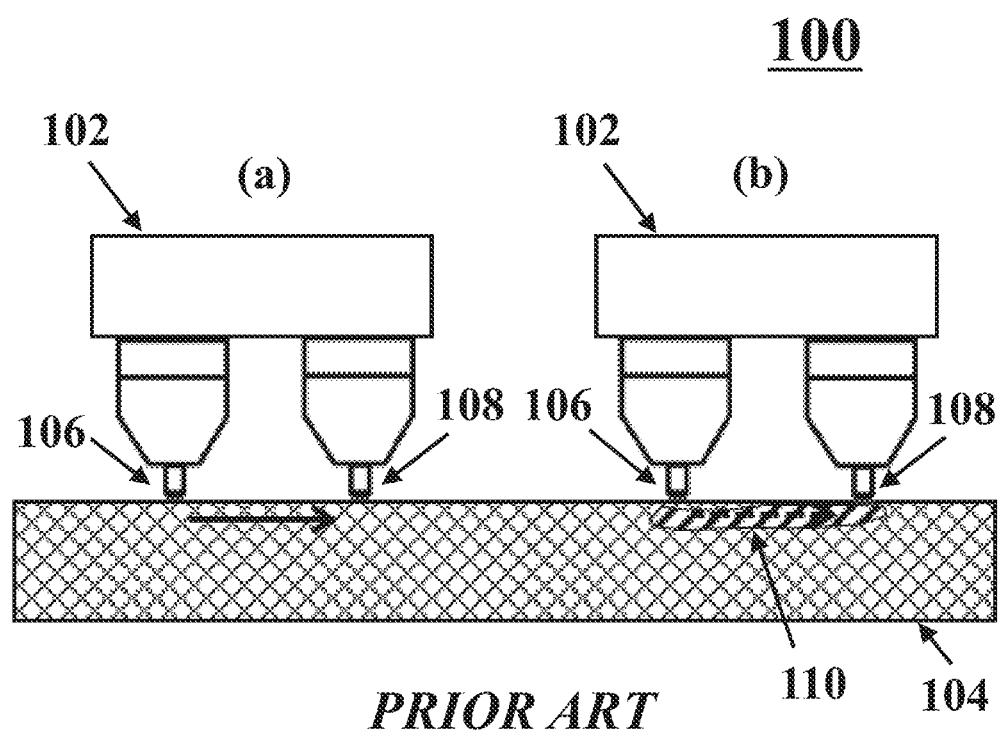
FIG. 1 is a front planar view of an apparatus for non-destructive testing of a composite structure.

Referring to FIG. 1, a front planar view 100 depicts a probe 102 operating as an apparatus for non-destructive testing of a composite structure 104. The probe 102 utilizes a conventional pitch-catch method wherein a Lamb wave is generated by the probe 102 while the probe 102 is in contact with the composite structure 104. A transmit piezoelectric device 106 of the probe 102 transmits the Lamb wave as an excitation signal into the composite structure 104 and a receive piezoelectric device 108 located at a predetermined distance from the transmit piezoelectric device 106 along the surface of the composite structure 104 receives Lamb wave reflections as a probed signal from the composite structure 104.

Those skilled in the art will understand that the behaviour of the Lamb wave in terms of wave mode, frequency, velocity, and level of attenuation highly depends on the material structures, thickness of the laminates and material properties of the composite structure 104. The repeatable, verifiable response to complex composite structures can be obtained if the excitation signal is probably selected. For example, the left side (a) of FIG. 1 depicts the probe 102 passing over a portion of the composite structure 104 having no defects. The right side (b) of FIG. 1 depicts the probe 102 passing over a portion of the composite structure 104 having a disbond defect 110.

Figure 2A:
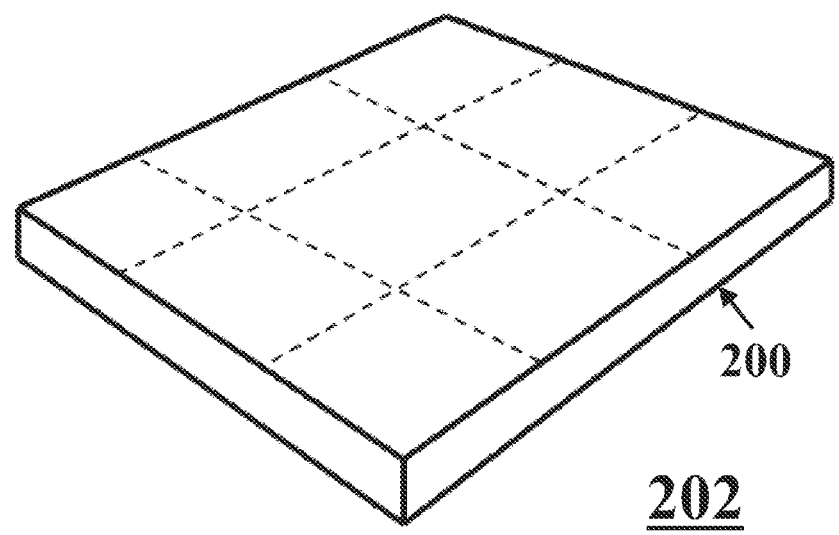
Figure 2B:
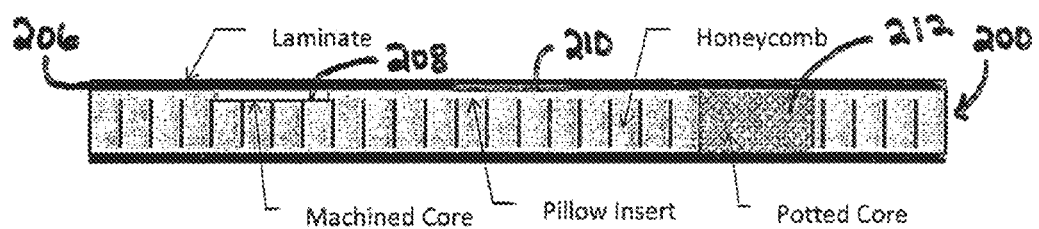

To determine the nature of the response, a reference composite structure 200 with known defects is tested. FIG. 2, comprising FIGS. 2A and 2B, depicts a typical reference composite structure 200 for equipment calibration. FIG. 2A is a left, top front perspective view 202 of the reference composite structure 200 and FIG. 2B is a front cross-sectional view 204 of the reference composite structure 200. In the cross-sectional view 204, an outer surface 206 of the reference composite structure 200 is made of a laminate material such as fiberglass or carbon fabric and covers the honeycombed inner structure. The reference composite structure 200 includes a number of predefined defects such as a machined core defect 208, a pillow insert defect 210, and a potted core defect 212 (which correspond respectively to the defects of disbonds, delaminations, and crushed core portions) for probing to develop a library of predetermined probed signals for comparison to actual defects.

Figure 3:
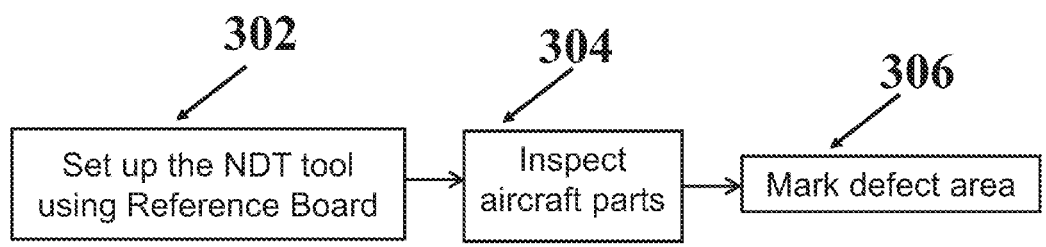
FIG. 3 is a flow diagram depicting an overview of the non-destructive composite structure testing method using the apparatus of FIG. 1.

Referring to FIG. 3, a flow diagram 300 depicts an overview of a conventional non-destructive composite structure testing method using the probe 102 (FIG. 1). At step 302, the system, which includes a tool to measure the signals from the probe 102, is initially set up by passing the probe 102 across the outer surface 206 of the reference composite structure 200 to generate a set of predetermined probed signals corresponding to the predefined defects 208, 210, 212 in the reference composite structure 200. The reference composite structure 200 includes engineered defect having types similar to those in the actual composite structures (e.g., aircraft structures) to be inspected. Also, the probe 102 and its operational mode (i.e., the excitation signal generation mode) should be selected in response to the shape and material of the actual composite structures. For example, a probe 102 which uses pitch-catch techniques may be more suitable for a first composite structure while a probe which uses resonance or mechanical impedance analysis (MIA) techniques may be more suitable for a second composite structure. Among the conventional inspection techniques, pitch-catch is the most commonly used as it is capable of detecting most defect types in the composite structures, including honeycomb composite structures. Conventional systems using the pitch-catch technique, however, may need several excitation signal transmissions before a defect is detected. This is typically determined during step 302.

Once the predetermined probed signals and the protocol for generating them are determined from step 302, the composite structure can be inspected 304 using the determined protocol and signals, and identified defect areas can be marked 306.

Figure 4:
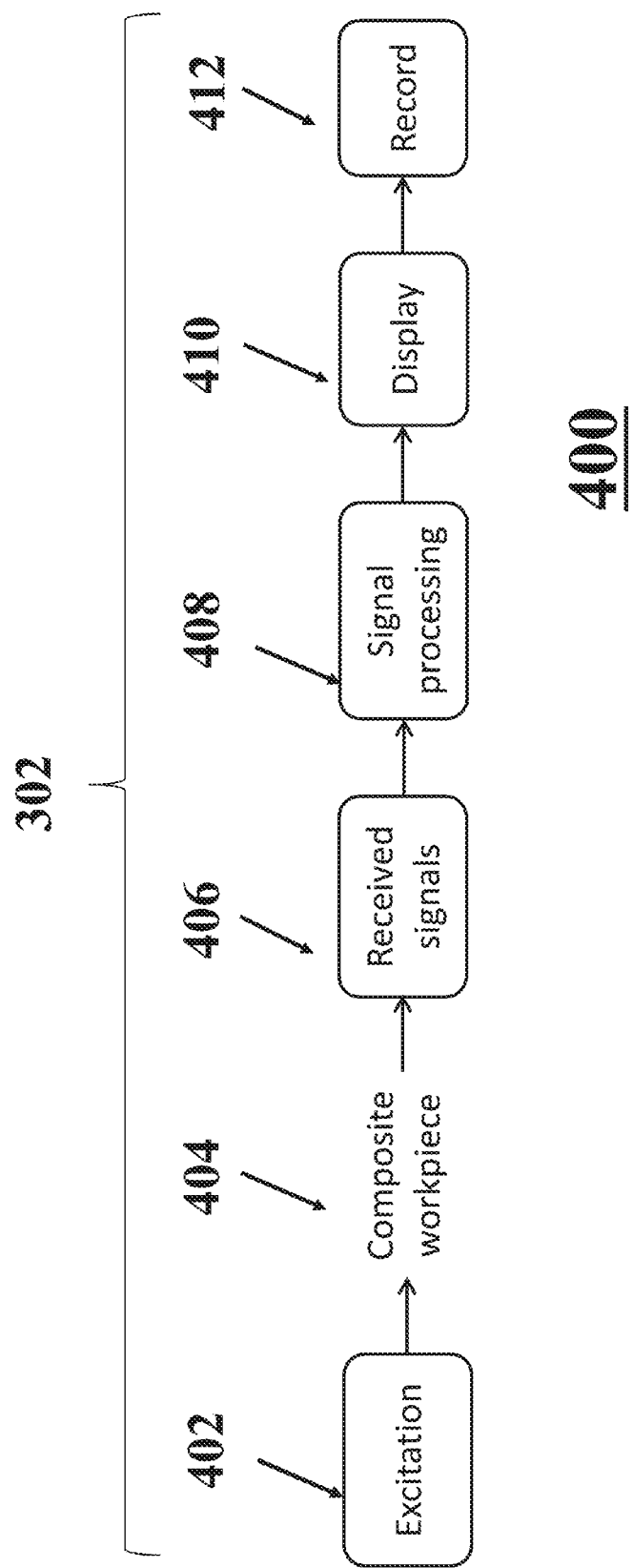
FIG. 4 is a flow diagram depicting an inspection portion of the non-destructive composite structure testing method of FIG. 3.

Referring next to FIG. 4 is a flow diagram 400 depicts the inspection portion 304 of the non-destructive composite structure testing method. Conventional pitch-catch inspection systems will have the capabilities of excitation generation, response acquisition, and processing, as well as information management for facilitating the inspection operation. The flow diagram 400 depicts the order of these, operations. Initially, an excitation signal is generated and provided 402 to the composite structure 404 (e.g., the composite structure 104 (FIG. 1)). The excitation signal provided at step 402 is an excitation signal appropriate to typical defects found in the particular type of composite structure 404. A probed signal, which is a response of the composite structure to the excitation signal provided at step 402, is received 406 and passes through a signal conditioning process 408 to be placed in a format where the defect features can be extracted before being presented (i.e., displayed) in a visual or graphical representation 410. The results may then be saved 412 for future reference.

Figure 5:
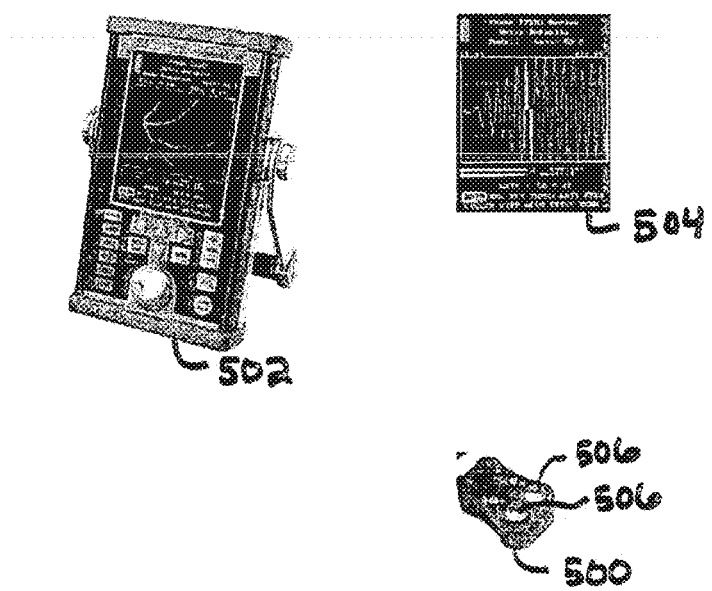
FIG. 5 is a front; right, top perspective view of components of a first conventional non-destructive composite structure testing system.
Figure 6:
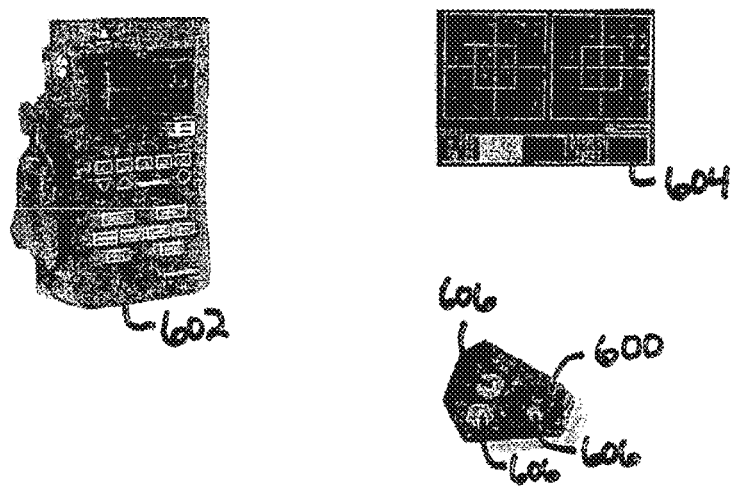
FIG. 6 is a front, left, top perspective view of components of a second conventional non-destructive composite structure testing system.

Since the introduction of the pitch-catch technique for non-destructive testing of composite structures in the 1980s, several products have become available in the market. These products include the BondaScope product manufactured by NDT Systems, Inc. of Huntington Beach, Calif., USA, shown in FIG. 5 (including a handheld probe 500 and a computing device 502 for processing and presenting the defect inspection information). A trace of an exemplary excitation signal is depicted in a graph 504 in FIG. 5. These products also include the BondMaster product manufactured by Olympus Corporation of Tokyo, Japan, shown in FIG. 6 (including a handheld probe 600 and a computing device 602 for processing and presenting the defect inspection information). A trace of an exemplary excitation signal is depicted in a graph 604 in FIG. 6. The probes 500, 600 are embedded with two piezoelectric elements for transmitting and receiving signal. The Lamb wave is introduced into the composite structure 104 by a piezoelectric element through a probe tip 506, 606. The wave can be excited through impulse mode, radio frequency mode, or swept mode to produce an appropriate excitation signal for defect detection. As the frequency is highly dependant on the composite structure and the type and size of the defects, a swept mode excitation through multiple frequencies of lower than 50 kHz is often used as a first try to detect any unknown defects. The probes 500, 600 are linked to the computing devices 502, 602 for providing received probed signals to the devices 502, 602 for data acquisition and data processing of received probed signals.

Figure 7A:
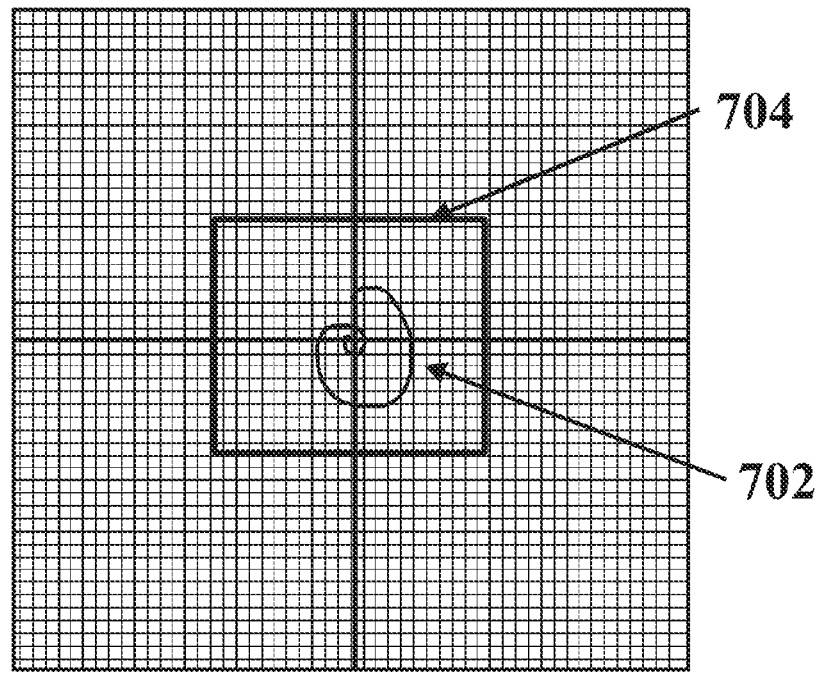
Figure 7B:
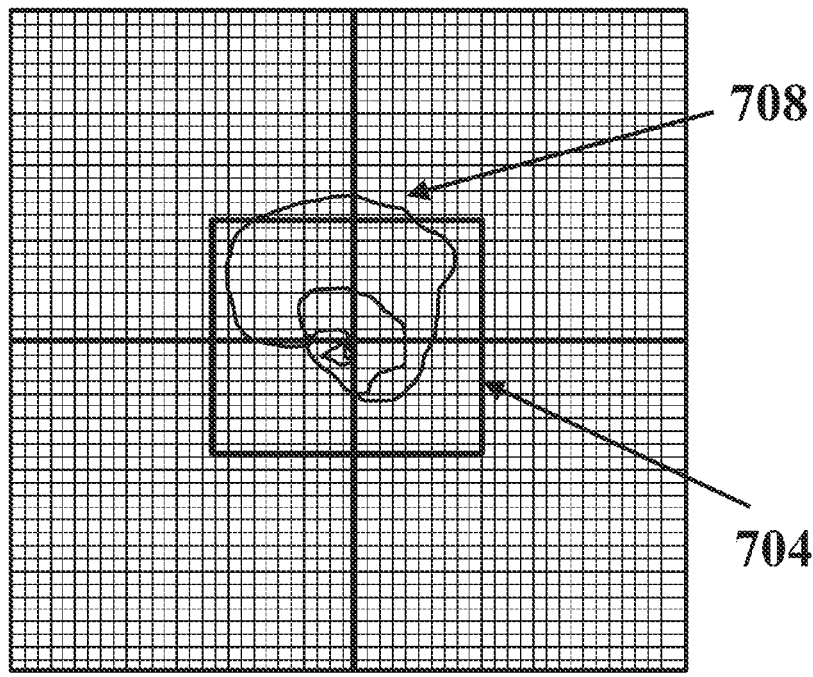

Referring to FIG. 7A, a graph 700 of the received probe signal of a trace 702 presented in the complex plane presents a circular closed or spiral-like trace 702 within a square box 704 when no defect is detected in the composite structure portion being tested. During the inspection operation, an operator will first obtain the response of the conventional device within a non-defect area. The operator will then set the square box 704 on a display to enclose the response curve. Thereafter, during inspection, as long as the response curve remains inside the square box 704, an operator can determine that the conventional inspection apparatus does not detect a defect. When, however, a curve 708 goes outside the square box 704, such as in the graph 710 of the received probe signal in FIG. 7B, the curve 708 indicates the pitch-catch probe 500, 600 has detected a defect (i.e., the curve 708 going outside the square box 704 depicting detection of a defect in the composite structure portion being tested). Thus, an experienced technician is required to interpret the displayed responses to the inspection for determining defect presence, location and size.

Accordingly, it can be seen that conventional non-destructive testing apparati have the following general technical and operational shortcomings, which are highly unfavourable to the maintenance, repair and overhaul (MRO) operations for the aircrafts: they are difficult to use, they are unable to indicate the type of defects, they are unable to identify the depth of the defects in the composite laminates in a single inspection, and they are unable, to scan portions of the composite structure to precisely locate a defect's size and/or geometry.

The success of detecting defects in composite structures depends on the excitation modes and the selection of response processing methods. The material conditions, in terms of properties, structures, size, and defect types will influence the response. Proper excitation has to be selected to get the maximum sensitivity to the defect type. Without knowing where and what types of defect, the inspection operation is tedious, time consuming and difficult.

While conventional non-destructive testing systems aim to be able to detect defects of different types, depth and size, presently existing systems typically are unable to distinguish the types of the defects and the depths of the defects. Such information is important during an inspection as some extent of the severity of the defects can be determined from the defect type and defect depth information. In addition, such information helps decide the type and/or nature of maintenance or repair actions, if any such actions are needed. Also, without accurate defect depth information, defects, such as delaminations in carbon fibre skins, can easily be mixed up or confused with other defects due to the size of the defect, leading to inefficient and/or ineffective repair processes.

Finally, conventional non-destructive testing systems include a handheld unit that typically does not perform in the same manner as a XY-stage scanner. Without the ability to accurately locate a position, geometry and/or boundary of a defect prohibits the recording of inspection results that are traceable for future reference, thus preventing assuring that no spot in the targeted inspection area is missing, that no area will be inspected twice, and, more importantly, preventing improved inspection visualisation and user friendliness of the inspection tools.

Figure 8:
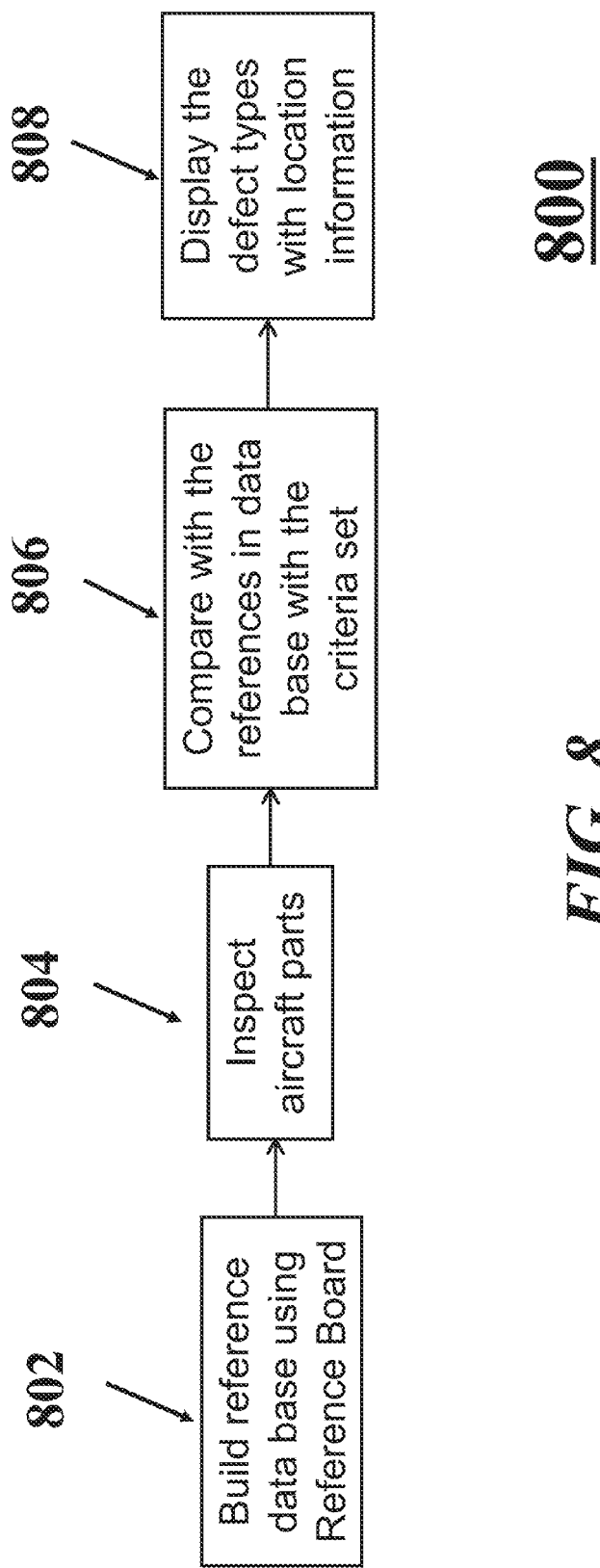
FIG. 8 is a flow diagram depicting an overview of the non-destructive composite structure testing method in accordance with a present embodiment.
Figure 9:
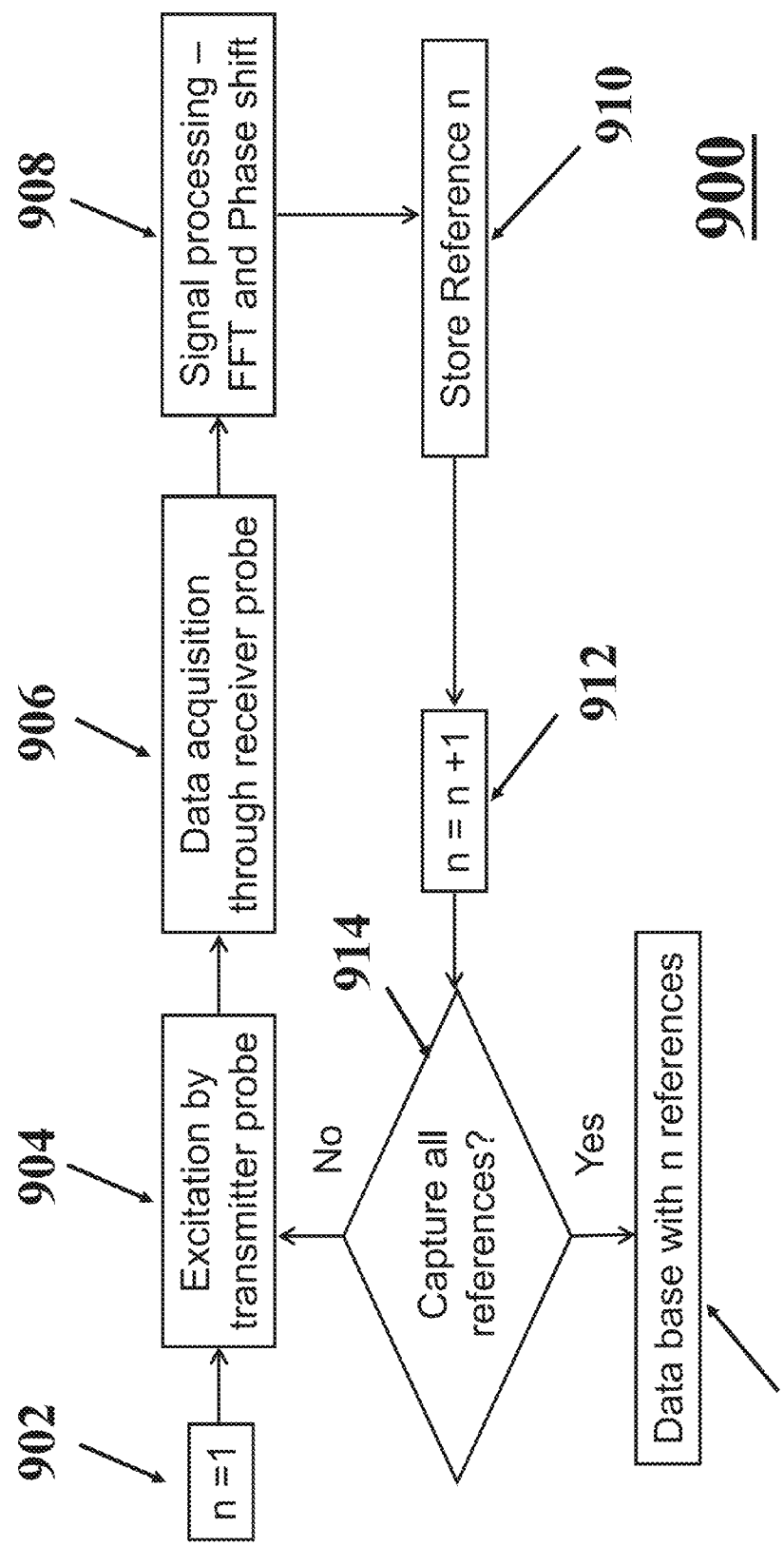
FIG. 9 is a flow diagram depicting a procedure for generating a library of predetermined probed signals for a reference composite structure of the non-destructive composite structure testing method in accordance with the present embodiment.

A present embodiment of the invention as described below overcomes these drawbacks of the prior art and presents a method and apparatus for detecting and identifying common defects in composite structures. The method includes the excitation signal design, feature extraction technique, defect identification and defect type visualization. The method and apparatus consist of a signal processing unit, ADC/DAC capabilities and a display. The apparatus works with a pitch-catch probe embedded with piezoelectric elements for guided Lamb wave generation and sensing. Referring to FIGS. 8 and 9, a first flow diagram 800 depicts an overview of the non-destructive composite structure testing method in accordance with the present embodiment and a second flow diagram 900 depicts a procedure for generating 802 a library of predetermined probed signals for a reference composite structure 200 of the non-destructive composite structure testing method in accordance with the present embodiment.

The method of identifying the defects in accordance with the present embodiment and depicted in FIG. 8 is by way of direct comparison of processed features. Responses of targeted, predefined defects is acquired at step 802, wherein a library of predetermined probed signals is acquired, processed and saved in a data base. During inspection 804, one or more probe tips transmit excitation signals to the composite structure being inspected and probed signals are received at the surface of the composite structure. The probed signals are correlated with (i.e.; compared with) 806 the library of predetermined probed signals and defect type information, defect location information and/or defect size information is determined and displayed 808.

Therefore, during building 802 the reference data base and carrying out the actual inspection 804, the method and apparatus of the present invention includes an excitation signal production mode, a feature extraction mode, a feature identification mode and a defect visualization mode.

Referring back to FIG. 9, the flow diagram 900 for generating the library of predetermined probed signals initializes 902 a counter n to one and provides 904 an excitation signal from one or more transmitter probe tip(s). One or more receiver probe tip(s) are examined to see if they have acquired data (i.e., received probed signals) 906. The probed signals are then processed 908 through fast Fourier transformation (FFT) and/or phase shifting to derive 910 a reference n. The counter n is incremented by one 912 and processing determines 914 whether all of the references have been captured. If all references have been captured 914, an n size database is stored 916 as the library of predetermined probed signals. If, on the other hand, all references have not been captured 914, processing returns to provide 904 another excitation signal by transmission from a probe tip.

Figure 10A:
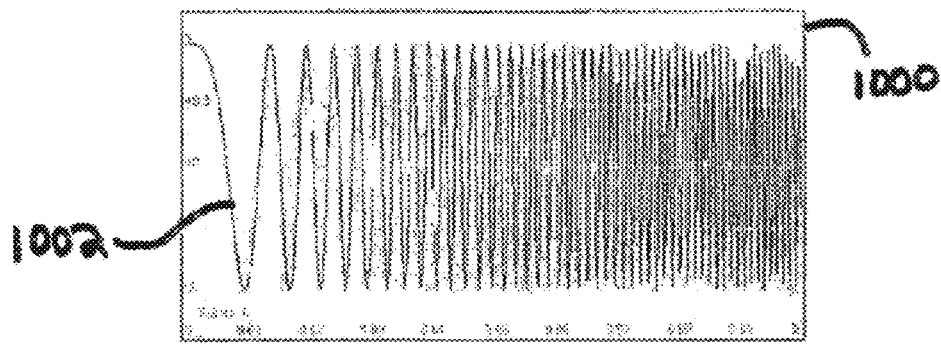
Figure 10B:
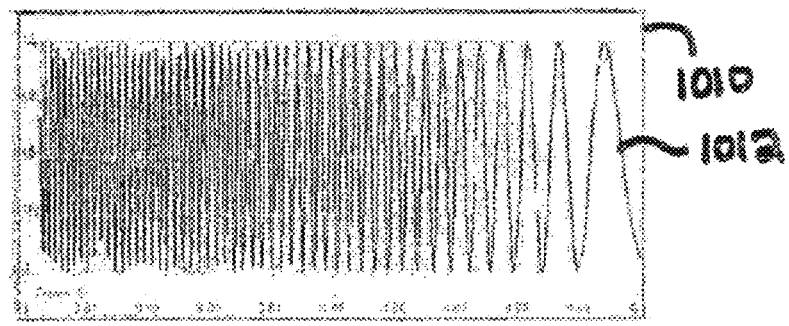
Figure 10C:
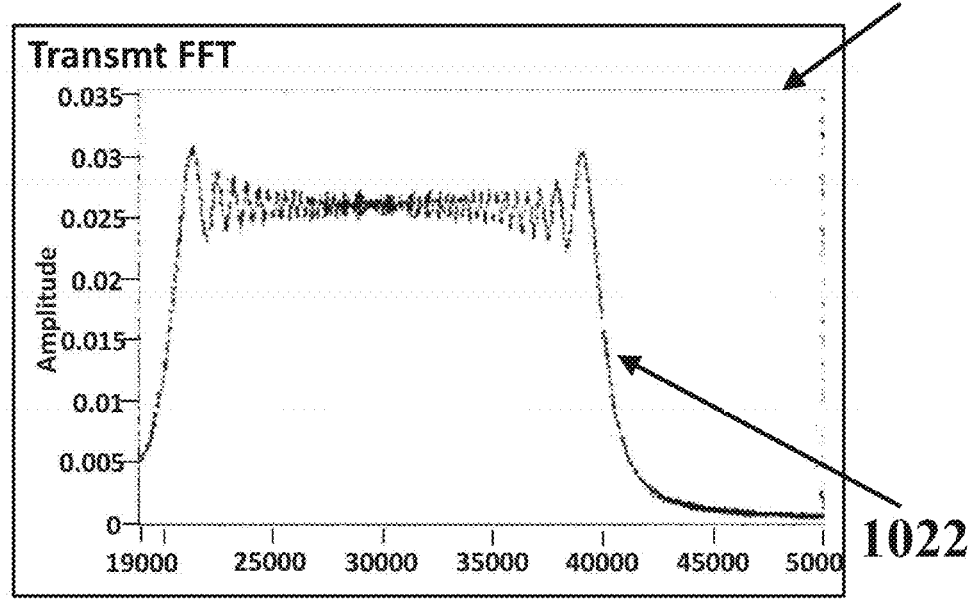

Both the library reference database building step 802 and the inspection step 804 involve an excitation signal production mode (e.g., step 904). In the excitation signal production mode in accordance with the present embodiment, a signal swept mode is utilized because it can capture a wide range of material conditions, including defect types and depth. The present embodiment differs from conventional signal swept modes in that the excitation signal is a linear chirp wave in which the frequency increases or decreases uniformly with time over a wide frequency band. Referring to FIG. 10, which includes FIGS. 10A, 10B and 10C, signaling diagrams of the wideband chirp excitation sweep signal of the non-destructive composite structure testing method 800 in accordance with the present embodiment is shown. FIG. 10A depicts a graph 1000 of the excitation sweep signals 1002 in accordance with the present embodiment wherein the sweep is over a twenty kilohertz (20 kHz) frequency range and increases from twenty kilohertz (20 kHz) to 40 kilohertz (40 kHz) within a predetermined time of three milliseconds (3 ms) in the time domain. FIG. 10B depicts a graph 1010 in the time domain which traces the excitation sweep signals 1012 in accordance with the present embodiment where the sweep is also over a twenty kilohertz (20 kHz) frequency range but the sweep decreases frequencies from 40 kilohertz (40 kHz) to twenty kilohertz (20 kHz) within a similar predetermined time of three milliseconds (3 ms). FIG. 10C depicts a graph 1022 of the excitation sweep signals in the frequency domain in accordance with the present embodiment where the sweep either increases or decreases in the range from twenty kilohertz (20 kHz) to 40 kilohertz (40 kHz) within a predetermined time of three milliseconds (3 ms).

The total predetermined time of the excitation signal is less than ten milliseconds (10 ms) and is preferably approximately three milliseconds (3 ms). The peak-to-peak amplitude of the excitation signal is a value in the range from one volt to one hundred volts and selection of the voltage is determined in response to the thickness of the laminates 206 (FIG. 2) of the composite structure as the signal needs to pass through the laminates 206 to detect any defects underneath.

As stated above in regards to FIG. 10, the frequency sweep is over a wide frequency band and either decreases or increases across the frequency band. The reason for using a decreasing chirp wave frequency decreasing from fifty kilohertz (50 kHz) to ten kilohertz (10 kHz) (or in a narrower frequency band from forty kilohertz (40 kHz) to twenty kilohertz (20 kHz)) is for addressing the dispersal nature of the Lamb wave wherein high frequency waves travel faster than low frequency waves in certain mode. As such, increasing or decreasing the signal generates waves of different frequencies that will not interfere with each other. In addition, the linear and uniform frequencies permit all of the frequencies to be treated equally in term of intensity so that the response to any material conditions (e.g., defects) will be prominently detectable. In accordance with the present embodiment, the predetermined time of the excitation signal production is much shorter than conventional excitation times which advantageously minimize the dispersal effect of the Lamb wave and the trailing effects possibly caused by boundary reflections. Accordingly, the excitation signal in accordance with the present embodiment provides a wideband chirp wave generated over a period of a few milliseconds at high amplitude voltage (up to 100 V peak-to-peak).

The response of the excitation signal wave after it passes through the material is processed into the form that is stable and repeatable for the material condition. In accordance with the present embodiment, the response signal received by the receiving probe (i.e., the probed signal) is processed into a stable and repeatable form by computing the phase shift fast Fourier transformations of the response signal over a range of frequencies. The phase shift of such response signal can be expressed as $$\text{Phase Shift} = \tan2^{-1}\left(\frac{\text{Im}\frac{FFT(x)_R}{FFT(y)_T}}{\text{Re}\frac{FFT(x)_R}{FFT(y)_T}}\right) \quad [1]$$

FFT( ) represents the Fast Fourier Transform of a real, one-dimensional time domain signal. In Equation [1], FFT $(y)_T$ is the one-dimensional time domain signal of the transmitted or the excitation signal and $FFT(x)_R$ is the Fast Fourier Transform of the received probed signal or response signal.

Figure 11:
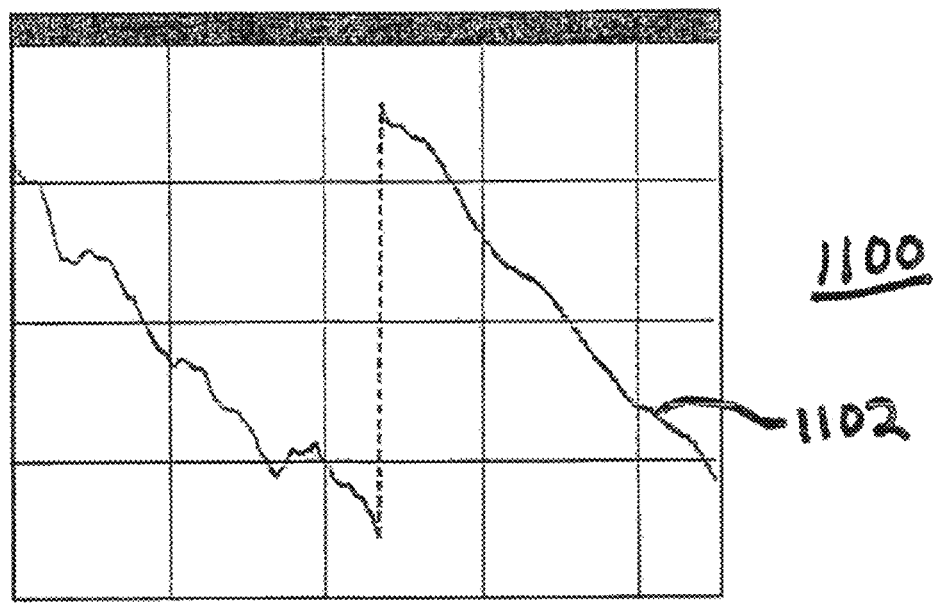
FIG. 11 is a graphical depiction of a phase shift profile of the received probe signal as plotted against the excitation signal over a range of frequencies of the excitation signal in accordance with the present embodiment.

Referring to FIG. 11, a graph 1100 depicts a phase shift profile 1102 of the received probe signal as plotted against the excitation signal over a range of frequencies of the excitation signal in accordance with the present embodiment. The defect type or material condition is identified based on the distinct processed responses recorded during the reference data base building stage 802, 900. Using the excitation signal and the method for processing the received signal, distinct phase shift profiles can be distinguished for various material conditions and defects (such as defect type information and defect depth information, as well as intact, non-defect areas) in the reference composite structure, such as the reference composite structure 200. A reference data base including a library of predetermined probed signals can be built (i.e., defined) during the reference data base building stage 802, 900. In this manner, defect responses (i.e., the probed signals) are collected, processed for the phased shift profile, and saved in the memory as the predetermined probed signals for the reference composite structure 200 for all types of defects contained therein.

Another method for processing response signals includes obtaining magnitudes of fast Fourier transformations (FFT) of the received probed signals. The magnitudes can be calculated as follows $$\text{Magnitude}(x) = |FFT(x)_R| = \sqrt{[\text{Re}[FFT(x)]]^2 + [\text{Im}[FFT(x)]]^2} \quad [2]$$

Figure 12:
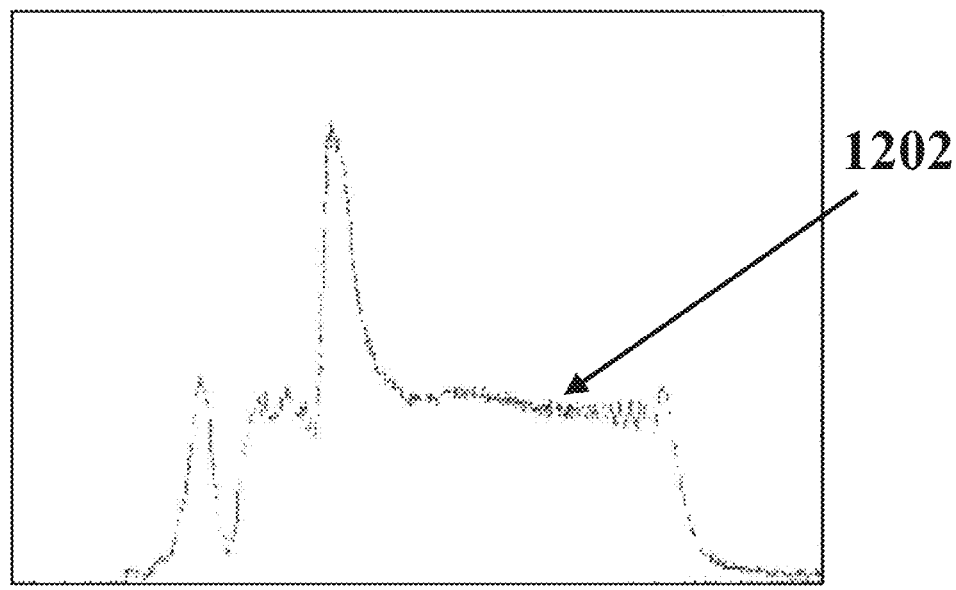
FIG. 12 is a graphical depiction of a phase shift profile of magnitudes of fast Fourier transformations (FFT) of the received probe signal as plotted against the excitation signal over a range of frequencies of the excitation signal in accordance with the present embodiment.

FIG. 12 depicts a graph 1200 of a phase shift profile 1202 of magnitudes of fast Fourier transformations (FFT) of the received probe signal as plotted against the excitation signal over a range of frequencies of the excitation signal in accordance with the present embodiment.

Figure 13A:
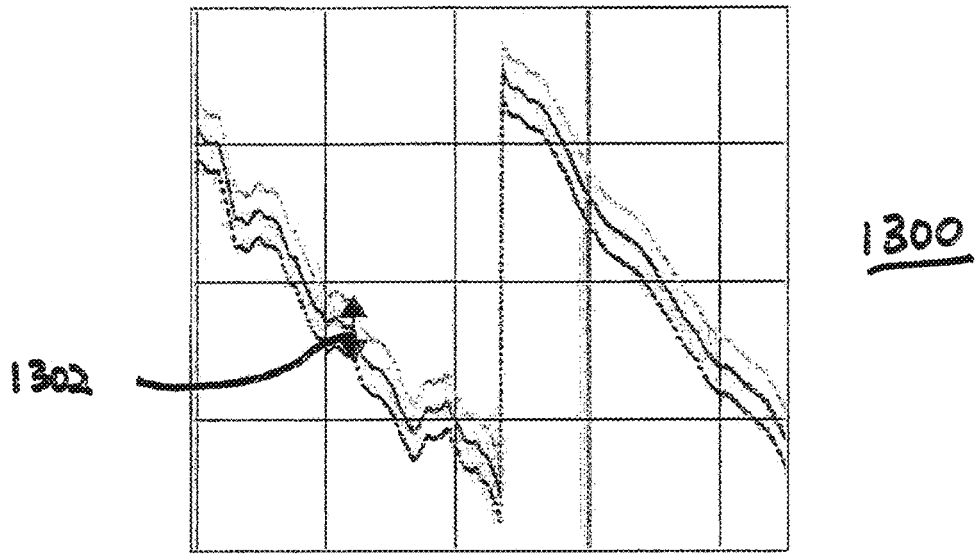
FIG. 13A is a graphical depiction of a phase shift profile of a predetermined received probe signal of a known defect as plotted against the excitation signal over a tolerance range of frequencies in accordance with the present embodiment and FIG. 13B is a graphical depiction of a phase shift profile of a received probe signal as plotted against the excitation signal while detecting several defects, including the known defect depicted in FIG. 13A in accordance with the present embodiment.
Figure 13B:
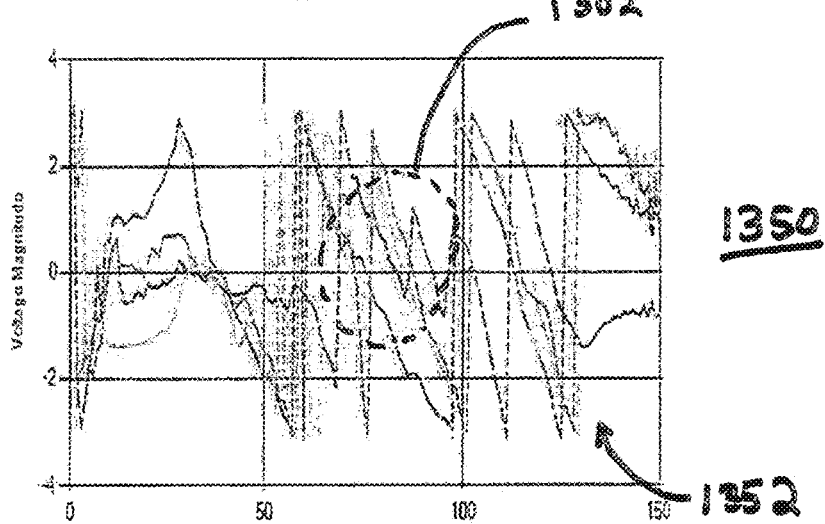

FIG. 13A is a graph 1300 of a phase shift profile of a predetermined received probed signal 1302 of a known defect as plotted against the excitation signal over a tolerance range of frequencies in accordance with the present embodiment for storage as a predetermined probed signal for storage in the reference data base. FIG. 13B is a graph 1350 of a phase shift profile of a received probed signal 1352 as plotted against the excitation signal while detecting several defects, including the phase shift profile 1302 of the known defect depicted in FIG. 13A in accordance with the present embodiment.

After the responses for all the defects are saved, a tolerance band is set for each of the phase shift profiles collected for the different material conditions (i.e., the predetermined probed signals indicative of different defects). The size of the tolerance band can be adjusted to suit the accuracy and sensitivity requirements for defect identification. The received probed signals collected during the inspection stage 804 (FIG. 8) are compared with the phase shift profile and/or the magnitude profile in real time during the actual inspection. A defect type can thus advantageously be determined based on the best match of the profile within the tolerance band set during the reference data base building stage 802, 900.

Figure 14:
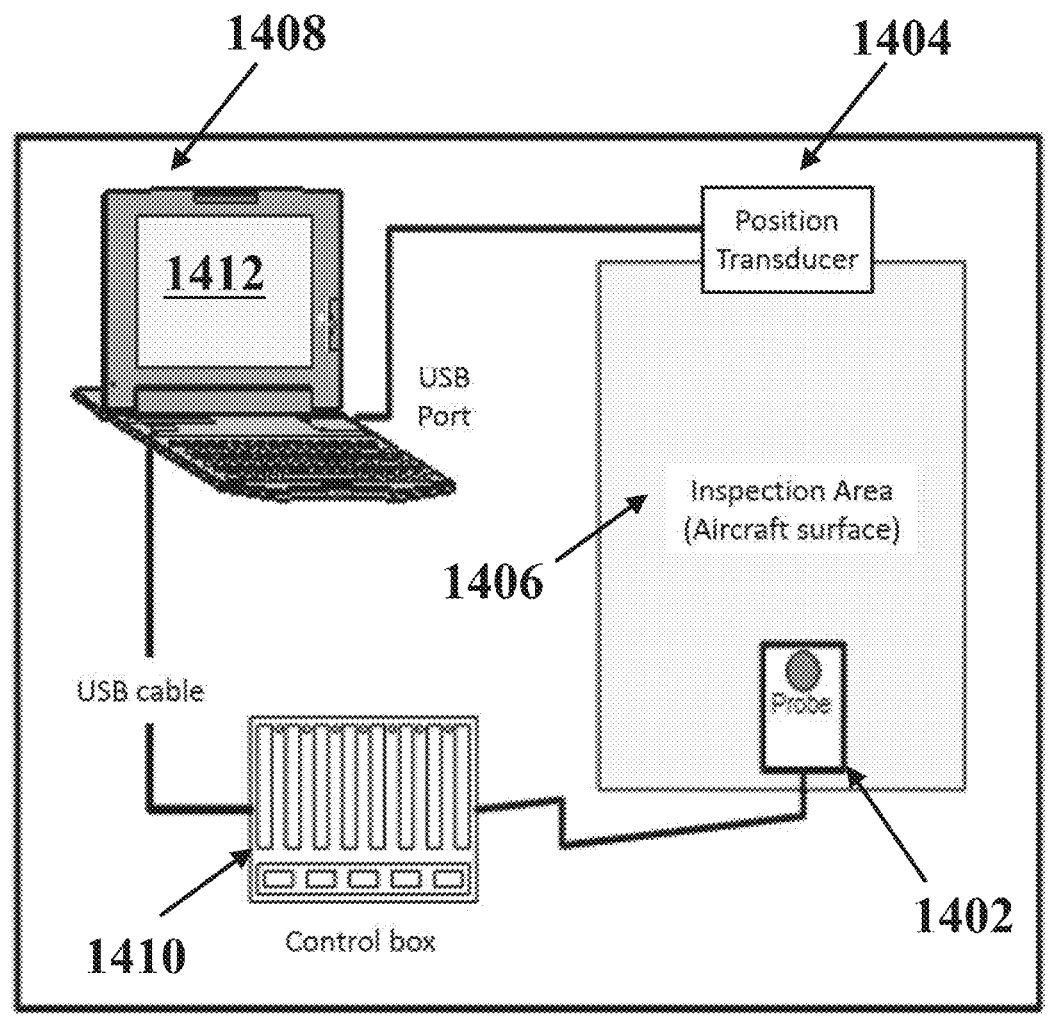
FIG. 14 is a block diagram of a non-destructive testing system in accordance with the present embodiment.

FIG. 14 depicts a block diagram 1400 of a non-destructive testing system in accordance with the present embodiment. The system includes a probe 1402 imbedded with a position transducer and a position sensor/encoder 1404 which cooperatively signal each other across an inspection area 1406 to generate information for processing by the computer 1408 for determination of defect size information, defect type information and defect location information from the excitation signals and the probed signals. A control box 1410 allows operator control of the method for inspection and defect identification of the system. The method comprises defining an inspection area before the actual inspection 804. The position sensor/encoder 1404 is attached to the aircraft surface (i.e., the surface of the composite structure) and the inspection probe 1402 is imbedded with a position transducer so that the actual inspection area on the aircraft (i.e., position of the probe 1402) is mapped onto the user interface (i.e., display screen) 1412 of the system to present a graphical or visual representation of defects detected.

Figure 15:
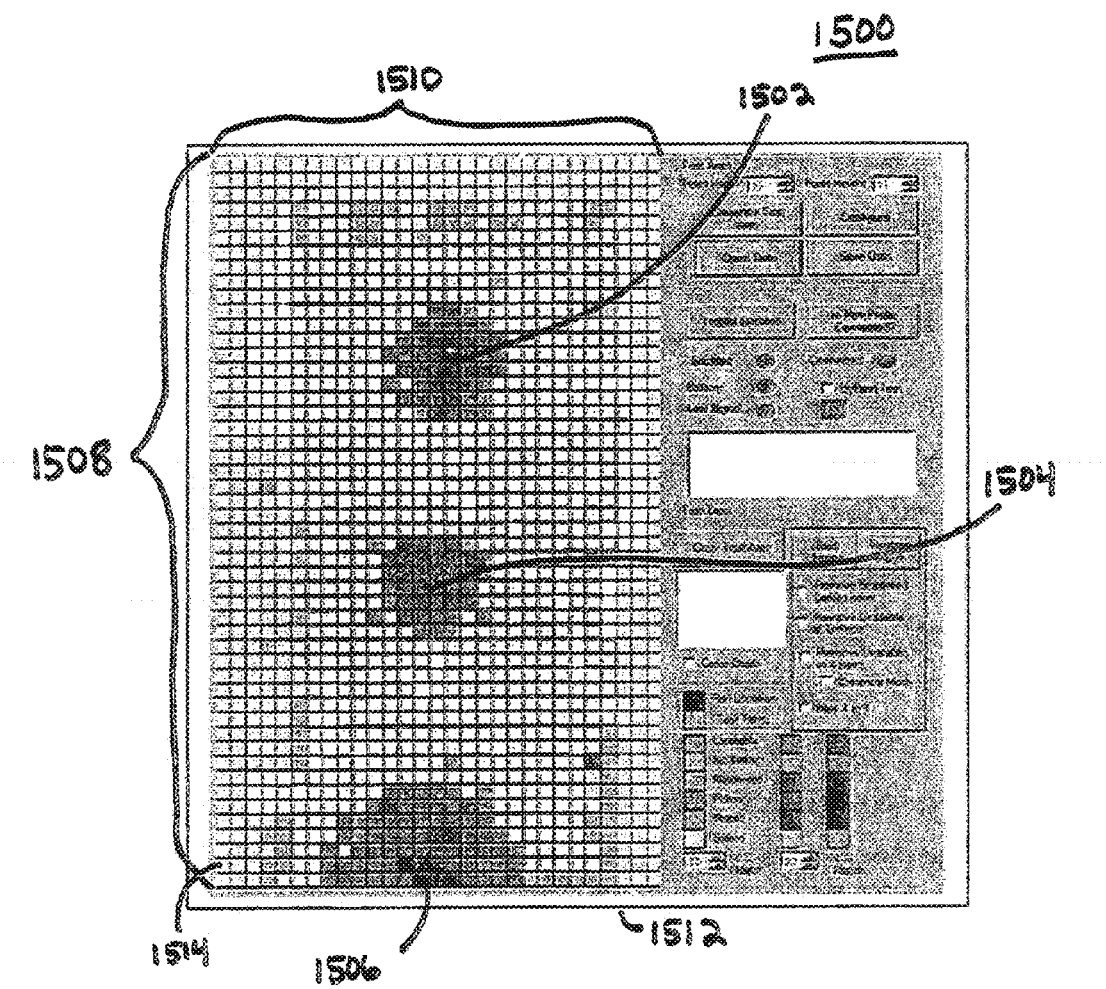
FIG. 15 is a graphical representation of defects detected as presented by the system of FIG. 14 in accordance with the present embodiment.

Those skilled in the art will realize that the position sensor/encoder 1404 and the probe 1402 transducer allow the linear coordinates of the probe 1402 relative to a defined frame on the aircraft surface to be determined. Referring to FIG. 15, a graphical representation 1500 of defects 1502, 1504, 1506 detected are presented by the system of FIG. 14 in accordance with the present embodiment. As can be seen in FIG. 15, the area to be inspected can be gridded with a user-chosen number of uniform rows 1508 and columns 1510 to form a display panel 1512 comprised of a number of grid boxes 1514. Each of the grid boxes 1514 is utilized to display the inspection result of the corresponding points on the actual aircraft surface. In the actual inspection operation, the user scans the inspection area 1406 with the probe 1402 and the processed results are displayed bit by bit in the grid boxes 1514. The results of the inspections are illustrated with visual parameters such as shapes or colors corresponding to the defect types assigned during the reference data base building stage 802, 900 to convey information such as defect location information, defect size information and/or the defect type information.

Thus it can be seen that the present embodiment is capable of identifying defect types and depths in composite structures and can generate a grid-based map of inspection areas with a handheld non-destructive testing apparatus. The present embodiment also advantageously allows the inspection scan results to be generated efficiently and saved for future use, thereby greatly enhancing the maintenance, repair and overhaul (MRO) operations for aircraft composite structures. Compared with conventional non-destructive testing for composite structures, methods and apparati in accordance with the present embodiment are able to detect and identify many defect types and clearly and effectively illustrate the inspection results on a display screen, including information on location, geometry and types of defects. While the results can be obtained by manually scanning the surface area, the method can be implemented on either a hand-held system for manual inspection or a X-Y stage for automated inspection.

Figure 16:
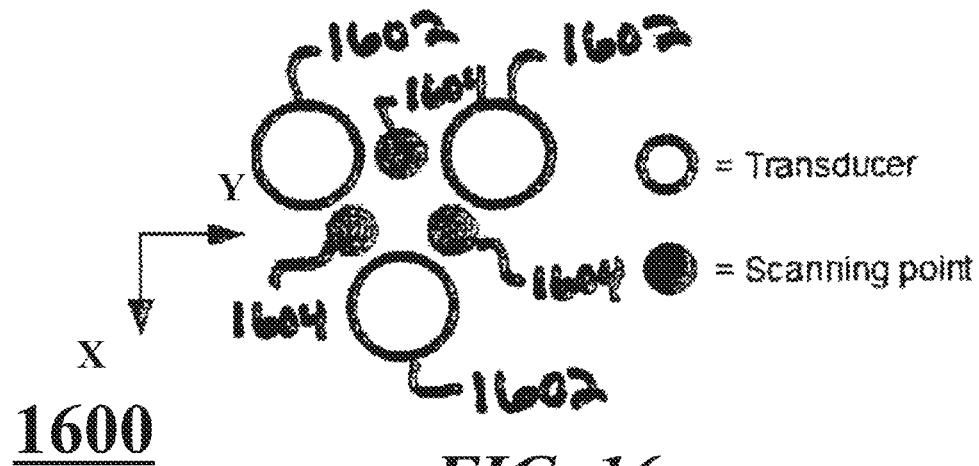
FIG. 16 is a diagram of a first geometry of transducers on a probe for use in the system of FIG. 14 in accordance with the present embodiment.

Referring to FIG. 16, a diagram 1600 of a first geometry of transducers on a probe for use in the system 1400 in accordance with the present embodiment is shown. A probe for an in-service non-destructive test for the aerospace industries based upon the pitch-catch probe (which can be utilized in both isotropic materials, such as aluminum, as well as in anisotropic materials, such as carbon fiber or glass fiber composite) includes transducers 1602 in a two-dimensional transducer arrangement where the distance between each adjacent transducer is equal. FIG. 16 shows the alignment of the transducers 1602 with scanning point/lines 1604, wherein three transducers 1602 are depicted. Each of the transducers 1602 is separately configurable as a transmitter for transmitting excitation signals or as a receiver for receiving probed signals.

Figure 17:
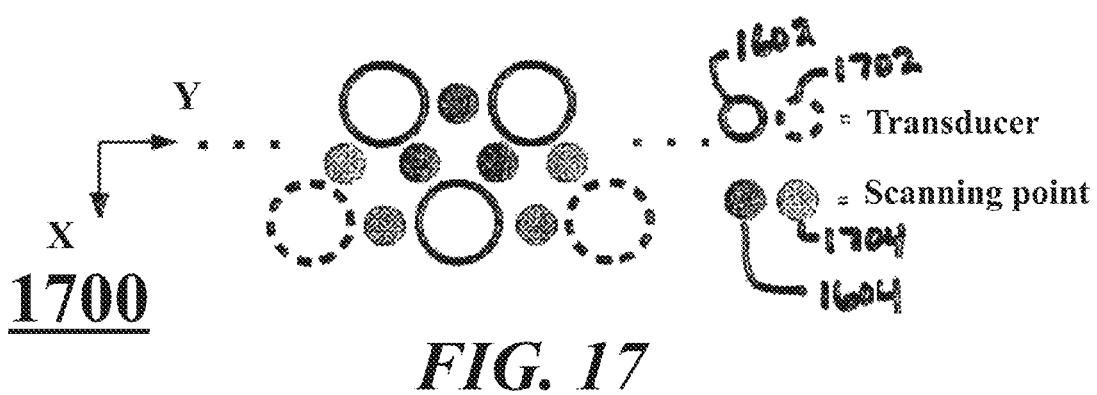
FIG. 17 is a diagram of a second geometry of transducers on a probe extending the arrangement depicted in FIG. 16 in accordance with the present embodiment.

FIG. 17 is a diagram 1700 of a second geometry of transducers 1602, 1702 on a probe extending the arrangement depicted in FIG. 16 in accordance with the present embodiment. FIG. 17 shows the flexibility of the probe design in accordance with the present embodiment for future addition of transducers. It can be seen in the diagram 1700 that with each additional transducer 1702, two scanning points 1704 can be obtained.

Figure 18:
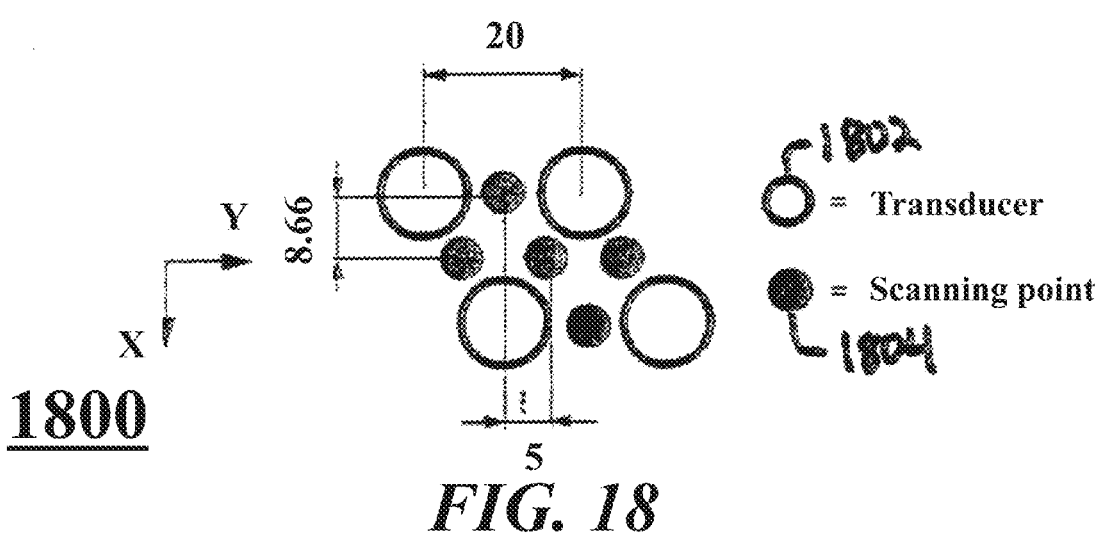
FIG. 18 is a diagram of a third geometry of transducers on a probe for use in the system of FIG. 14 in accordance with an alternate embodiment.

FIG. 18 is a diagram 1800 of a third geometry of transducers 1802 on a probe for use in the system of FIG. 14 in accordance with an alternate embodiment and includes distances between the transducers 1802 and the distance between the scanning points 1804. This third geometry depicted in FIG. 18 includes four transducers 1802 located to form a rhombus shape.

Figure 19:
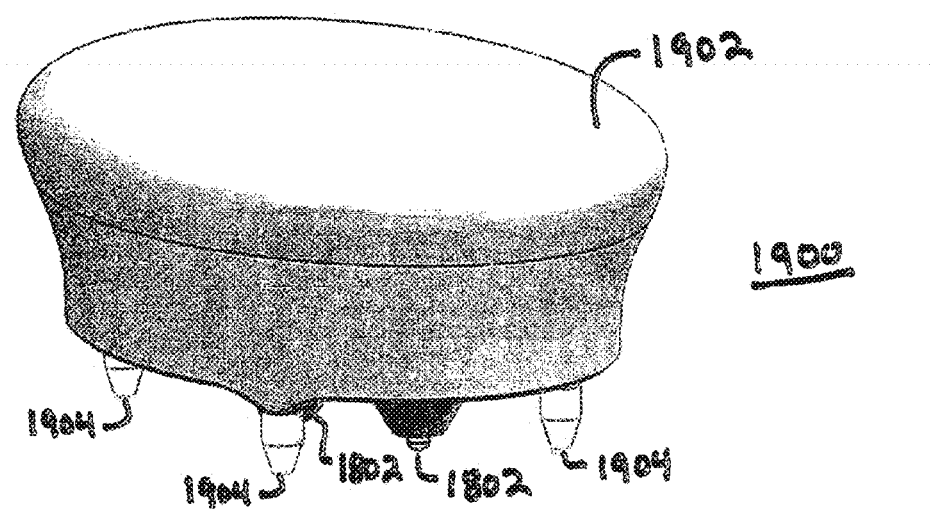
FIG. 19 a front, right, top perspective view of a handheld probe for use in the system of FIG. 14 in accordance with the alternate embodiment.

Referring next to FIG. 19 a front, right, top perspective view 1900 of a handheld probe for use in the system of FIG. 14 in accordance with the alternate embodiment includes a housing 1902. The transducers 1802 can be seen projecting from the bottom of the probe and supporting legs 1904 help maintain the probe in a fairly even, upright position throughout an inspection scan and at an even distance from the surface of the composite structure being scanned. The supporting legs 1904 further ensure balance of the probe and prevent the transducers 1804 from being over-pressed while during the inspection scan.

Figure 20:
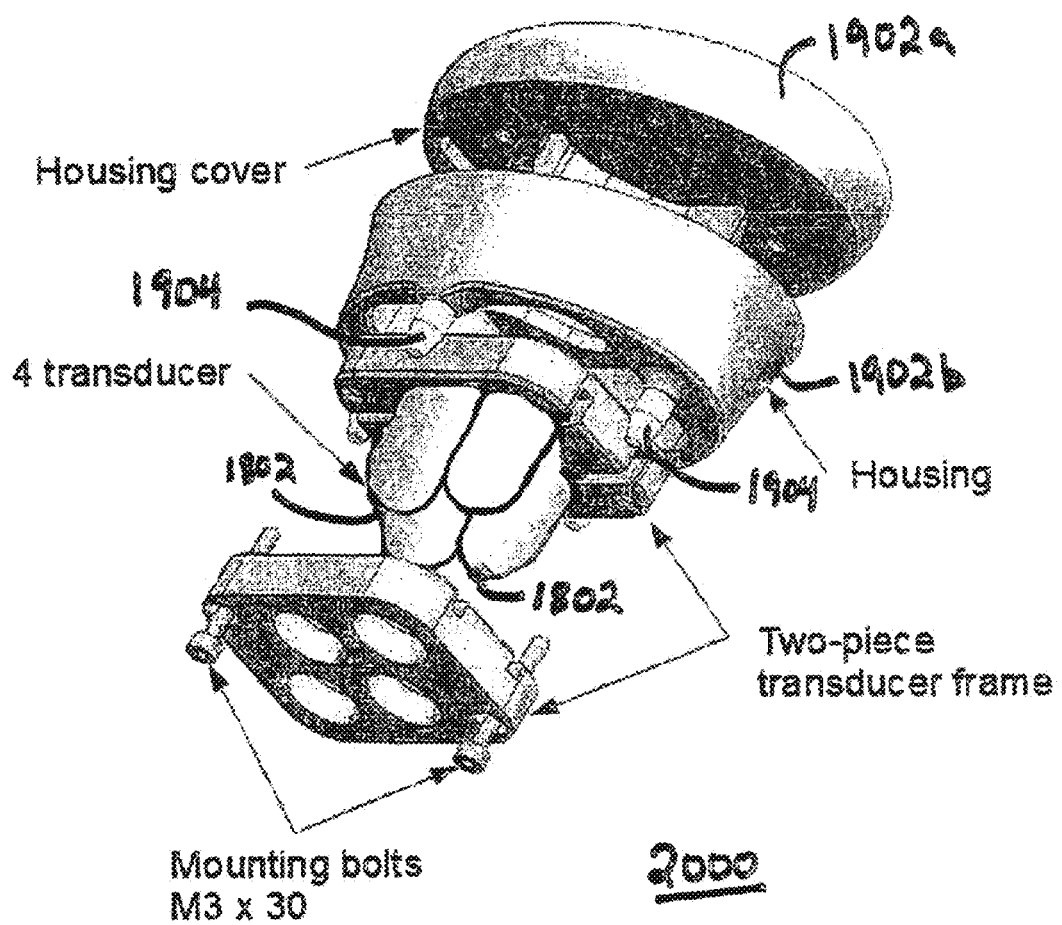
FIG. 20 a bottom, left, front exploded perspective view of the handheld probe of FIG. 19 in accordance with the alternate embodiment.

FIG. 20 depicts a bottom, left, front exploded perspective view 2000 of the handheld probe of FIG. 19 in accordance with the alternate embodiment. The view 2000 shows the modular design of the array probe housing to allow flexibility in replacing and modifying parts of the housing.

Figure 21:
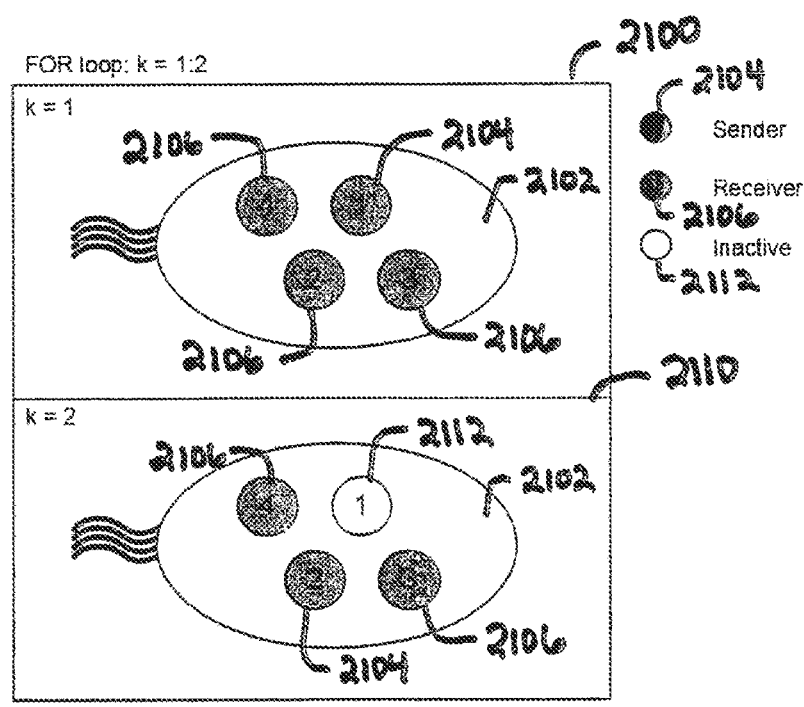
FIG. 21 a pair of transducer configuration diagrams illustrating transmitter and receiver assignment of the transducers in an array of transducers during operation of the system of FIG. 19 in accordance with the alternate embodiment.

FIG. 21 includes a pair of transducer configuration diagrams 2100, 2110 illustrating transmitter and receiver assignment of the transducers in an array 2102 of transducers during operation of the system of FIG. 19 in accordance with the four transducer alternate embodiment. In the first iteration 2100, transducer (1) acts as a transmitter 2104 while transducers (2), (3), and (4) act as receivers 2106. The next iteration 2110, transducer (2) acts as a transmitter 2104 while transducers (3) and (4) remain as receivers 2106. In this stage, transducer (1) actually behaves as a receiver; however the recorded signal can be ignored due to the similarity from the first iteration and so transducer (1) is treated as an inactive transducer 2112.

The four transducer array probe is capable of inspecting multiple scan points/lines at one time thus reducing inspection time. Further it is capable of addressing fiber orientation in composite materials and more accurately determining the probability of a defect. The four transducer array reduces overlapping of scanned areas and, correspondingly, reduces missing spots or uninspected areas.

As can be seen from FIGS. 16 to 18, the three or more transducers in the array probe are arranged systematically where the distances from one transducer to the adjacent ones are equal. Such arrangement ensures that the wave propagation distance between the transmitter and the receiver is the same, which allows flexibility of the transducers to be reconfigured as transmitters or receivers. It can also be seen that such arrangement allows future transducer addition to be incorporated without significant modification to the algorithm. For each additional transducer, two measurement points can be obtained with the proposed arrangement.

The array probe housing 1902 is designed to provide user comfort during operation and scanning. The round-shaped outer housing 1902 is designed to fit comfortably in an adult human hand. In addition, the housing 1902 is designed in modules to allow flexibility in design modifications as depicted in FIG. 20. Therefore, any changes to the transducer arrangement do not require the entire housing to be redesigned.

The proposed arrangement of the transducers, as well as the reconfigurability of each transducer as a transmitter or receiver, allows up to five (5) measurement points/lines to be obtained from each run. Referring to iteration 2100, transducer one (1) is configured as a transmitter 2104, while the others are configured as receivers 2106. In the second iteration 2110, transducer two (2) is configured as a transmitter 2104 while transducers three (3) and four (4) remain as receivers 2106. In the second iteration 2110, transducer one (1) acts as a receiver 2106, but the received signal can be ignored Compared with the conventional pitch-catch probes, a key unique feature of the transducer array probe in accordance with the present and alternate embodiments is the use of multiple transducers (i.e., three or more transducers), which are systematically arranged to achieve the optimal performance in terms of scan time and efficiency. As a result, multiple measurements can be obtained from a single excitation. The proposed transducer arrangement maintains the same distance from each transducer, which allows the flexibility to interchange the transmitting and receiving process. In addition, the placement of the transducers is such that the array probe is able to address the fiber orientation in composite materials. Another benefit of using the array probe is a higher degree of confidence in determining a defected area. In particular, measurement results can be aggregated and used to statistically determine the probability of a defect. Lastly, the use of the array probe in accordance with the present and/or alternate embodiments along with an automated process reduces the chances of uninspected spots, while maintaining reasonable scan time.

Thus, an probe for performing one-sided non-destructive testing for aircraft composite materials in accordance with the alternate embodiment of FIGS. 18 to 21 includes four (4)

transducers, spaced twenty millimeters (20 mm) apart from one another and arranged to form two isosceles triangles; four (4) support legs; and a modular housing design to allow flexibility in future modifications. A probe in accordance with this alternate embodiment can achieve faster scanning as compared to traditional pitch-catch probe by, in addition to other benefits, reducing overlapping in scanned areas. Such probes can also achieve a high probability of defect detection due to the multiple scanning points, and achieve more accurate scan due to the reduction of missed areas. Further, such probes can address fiber orientations of the composite materials due to the angled placement of the transducers.

While probes designed in accordance with the present and/or alternate embodiments are well suited for aircraft maintenance, repair, and overhaul (MRO), they may also be used for inspections in other applications, such as welding and joint inspections.

Thus it can be seen that a method and apparatus for Lamb wave-based non-destructive testing of composite structures which distinguishes between a variety of defects types not previously distinguishable and which provides a more user-friendly presentation of test results has been disclosed which advantageously provides a more efficient, accurate and user-friendly inspection process for detecting defects in composite structures. While at least one exemplary embodiment has been presented in the foregoing detailed description of the invention, it should be appreciated that a vast number of variations exist, including a vast number of probe designs that are useful for such method and apparatus.

It should further be appreciated that the exemplary embodiment or exemplary embodiments are only examples, and are not intended to limit the scope, applicability, dimensions, or configuration of the invention in any way. Rather, the foregoing detailed description will provide those skilled in the art with a convenient road map for implementing an exemplary embodiment of the invention, it being understood that various changes may be made in the function and arrangement of elements and method of play steps described in an exemplary embodiment without departing from the scope of the invention as set forth in the appended claims.

What is claimed is:

1. A method for non-destructive testing of a composite structure comprising:
providing a wideband chirp wave sonic signal to the composite structure for a predetermined time having a predetermined amplitude and a predetermined range of frequencies as an excitation signal;
correlating a probed signal received from the composite structure with a library of predetermined probed signals, the library of predetermined probe signals comprising probe signals received from a reference composite structure generated in response to the wideband chirp wave sonic signal provided to the reference composite structure for the predetermined time having the predetermined amplitude and the predetermined frequency, wherein the reference composite structure includes one or more predefined defects; and
outputting a graphical representation of defects detected, wherein the graphical representation of the defects detected conveys defect type information.

2. The method in accordance with claim 1 wherein the step of providing the wideband chirp wave sonic signal comprises providing the wideband chirp wave sonic signal to the composite structure as the excitation signal at a predetermined range of frequencies between twenty kilohertz (20 kHz) and forty kilohertz (40 kHz) with a frequency of the excitation signal either decreasing or increasing over the predetermined time.

3. The method in accordance with claim 1 wherein the step of providing the wideband chirp wave sonic signal comprises providing the wideband chirp wave sonic signal to the composite structure as the excitation signal having a predetermined high amplitude of less than one hundred volts peak-to-peak.

4. The method in accordance with claim 1 wherein the step of providing the wideband chirp wave sonic signal comprises providing the wideband chirp wave sonic signal to the composite structure for a predetermined time duration less than ten milliseconds as the excitation signal.

5. The method in accordance with claim 1 wherein the library of predetermined probed signals comprises a library of phase shift fast Fourier transformations of the probed signals calculated from the phase shift fast Fourier transformations of the probed signals received from the reference composite structure over a range of frequencies.

6. The method in accordance with claim 1 wherein the library of predetermined probed signals comprises predetermined probed signals generated in response to magnitudes of fast Fourier transformations of the probed signals received from the reference composite structure.

7. The method in accordance with claim 1 wherein the step of outputting the graphical representation of defects detected comprises outputting the graphical representation of defects detected, wherein the graphical representation of the defects detected convey defect size information, defect type information and the defect location information.

8. The method in accordance with claim 1 wherein the step of outputting the graphical representation of defects detected comprises outputting the graphical representation of defects detected, wherein a visual presentation of the graphical representation of the defects detected comprises one or more visual presentation parameters such as shape or color for conveying information including defect location information, defect size information or the defect type information.

9. The method in accordance with claim 1 wherein the step of correlating a probed signal comprises correlating a fast Fourier transformation of the probed signal received from the composite structure with the library of predetermined probed signals, wherein the library of predetermined probed signals comprises a library of phase shift fast Fourier transformations of probed signals received from the reference composite structure over a range of frequencies.

10. The method in accordance with claim 1 wherein the step of correlating a probed signal comprises correlating a magnitude of a fast Fourier transformation of the probed signal received from the composite structure with the library of predetermined probed signals, wherein the library of predetermined probed signals comprises a library of predetermined probed signals calculated in response to magnitudes of fast Fourier transformations of probed signals received from the reference composite structure.

11. An apparatus for non-destructive testing of a composite structure comprising:
a transmitter providing a wideband chirp wave sonic signal to the composite structure for a predetermined time, a predetermined amplitude and over a predetermined range of frequencies as an excitation signal;
a receiver for receiving a probed signal from the composite structure in response to the excitation signal;
a user interface for presenting a graphical representation of defects detected;

a storage device for storing a library of predetermined probed signals, the library of predetermined probe signals comprising probe signals received by the receiver from a reference composite structure including one or more predefined defects, the probe signals generated in response to a wideband chirp wave sonic signal produced by the transmitter to the reference composite structure for the predetermined time having the predetermined amplitude and the predetermined frequency, wherein a controller thereafter provides the library of predetermined probed signals to the storage device for storing therein; and the controller coupled to the receiver, the storage device and the user interface for correlating the probed signal received with the library of predetermined probed signals and providing signals to the user interface for outputting a graphical representation of defects detected conveying defect location information.

12. The apparatus in accordance with claim 11 wherein the controller is coupled to the transmitter and generates signals for providing thereto to provide the wideband chirp wave sonic signal to the composite structure as the excitation signal at a predetermined frequency range between twenty kilohertz (20 kHz) and forty kilohertz (40 kHz) with a frequency of the excitation signal either decreasing or increasing over the predetermined time.

13. The apparatus in accordance with claim 11 wherein the controller is coupled to the transmitter and generates signals for providing thereto to provide the wideband chirp wave sonic signal to the composite structure as the excitation signal having a predetermined high amplitude of less than one hundred volts peak-to-peak.

14. The apparatus in accordance with claim 11 wherein the controller is coupled to the transmitter and generates signals for providing thereto to provide the wideband chirp wave sonic signal to the composite structure for a predetermined time duration less than ten milliseconds as the excitation signal.

15. The apparatus in accordance with claim 11 wherein the controller provides signals to the user interface for outputting a graphical representation of defects detected conveying defect type information, defect size information and the defect location information.

16. The apparatus in accordance with claim 11 wherein the user interface presents a visual presentation of the graphical representation of the defects detected comprising one or more visual presentation parameters such as shape or color for conveying information including defect type information, defect size information or the defect location information.

17. The apparatus in accordance with claim 11 wherein the transmitter comprises one or more transmitters and the receiver comprises one or more receivers, the apparatus further comprising a probe coupled to the controller, the probe comprising three or more transducers separately configurable as either one of the one or more transmitters or one of the one or more receivers, and wherein each of the three or more transducers are equally spaced one from another, and wherein the controller is coupled to each of the three or more transducers for providing signals thereto and receiving signals therefrom, wherein the signals provided thereto include signals for configuring the transducers as either one of the one or more transmitters or one of the one or more receivers.

18. The apparatus in accordance with claim 17 wherein the probe comprises four transducers located on the probe to form a rhombus shape.

* * * * *